(12) United States Patent
Hilscher et al.

(10) Patent No.: US 8,256,979 B2
(45) Date of Patent: Sep. 4, 2012

(54) APPLICATION SUBSTANCE RESERVOIR FOR TOOTHBRUSHES AND ELECTRIC TOOTHBRUSH

(75) Inventors: Alexander Hilscher, Königstein/Taunus (DE); Christian Neyer, Eschborn (DE)

(73) Assignee: Braun GmbH, Kronberg (DE)

( * ) Notice: Subject to any disclaimer, the term of this patent is extended or adjusted under 35 U.S.C. 154(b) by 993 days.

(21) Appl. No.: 12/159,353

(22) PCT Filed: Dec. 14, 2006

(86) PCT No.: PCT/EP2006/012033
§ 371 (c)(1),
(2), (4) Date: Jun. 26, 2008

(87) PCT Pub. No.: WO2007/079897
PCT Pub. Date: Jul. 19, 2007

(65) Prior Publication Data
US 2009/0031510 A1 Feb. 5, 2009

(30) Foreign Application Priority Data
Dec. 30, 2005 (DE) .......................... 10 2005 063 196

(51) Int. Cl.
*A46B 11/04* (2006.01)
(52) U.S. Cl. .................. 401/270; 401/188 R; 401/278; 15/29; 15/167.1; 433/85; 433/89; 433/122
(58) Field of Classification Search .................. 401/187, 401/188 R, 270, 278, 279; 15/23, 24, 28, 15/29, 167.1; 433/84, 85, 89, 122, 131, 216
See application file for complete search history.

(56) References Cited

U.S. PATENT DOCUMENTS

| 6,902,337 | B1 | 6/2005 | Kuo |
| 7,401,373 | B2 * | 7/2008 | Tybinkowski et al. .......... 433/82 |
| 7,726,955 | B2 * | 6/2010 | Ryser et al. .................. 417/420 |
| 2003/0056307 | A1 | 3/2003 | Tybinkowski et al. |

FOREIGN PATENT DOCUMENTS

| DE | 23 43 421 | 3/1975 |
| DE | 102 25 232 | 12/2002 |
| DE | 101 59 395 | 6/2003 |
| EP | 0 930 960 | 8/2003 |
| WO | WO00/75491 | 12/2000 |
| WO | WO02/071970 | 9/2002 |
| WO | WO03/054771 | 7/2003 |
| WO | WO2005/122950 | 12/2005 |

* cited by examiner

*Primary Examiner* — Steven J Ganey
(74) *Attorney, Agent, or Firm* — John P. Colbert

(57) ABSTRACT

An application substance reservoir for a toothbrush is provided. The reservoir has a data carrier and may be filled with toothpaste or another application substance. An electric toothbrush is also provided. The data carrier of the application substance reservoir may contain, for example, information regarding the prevailing filling level of the application substance reservoir and the type of application substance. The electric toothbrush has a data receiver for reading the data stored in the data carrier, a data transmitter for writing to the data carrier, and a control unit which may display the filling level in the application substance reservoir or the particular application substance used.

25 Claims, 3 Drawing Sheets

APPLICATION SUBSTANCE RESERVOIR FOR TOOTHBRUSHES AND ELECTRIC TOOTHBRUSH

TECHNICAL FIELD

This disclosure relates to replaceable application substance reservoirs for toothbrushes, and to electric toothbrushes in which such reservoirs are used.

BACKGROUND

WO 03/054771 A1 describes an electric toothbrush consisting of a handpiece and a replaceable attachable brush. The attachable brush contains a memory in which information identifying the attachable brush is stored. The attachable brush also contains a transponder which outputs the information stored in the memory when it receives an inquiry signal from an inquiry station. The handpiece contains a microcontroller which calculates the cumulative use time of the attachable brush identified and can write this information into the memory of the attachable brush. The handpiece is also provided with a display with which the need for replacing an attachable brush can be displayed.

DE 10 2004 062150 describes a replaceable accessory part for an electric toothbrush and a method for determining the use time of the accessory part.

There are already known electric toothbrushes into which may be inserted a toothpaste bag from which toothpaste can be dispensed during operation of the toothbrush. The bag is replaceable, so that when it is empty, it can be replaced by a filled bag. Electric toothbrushes may also be used by multiple users, in which case each user can attach his own brush head onto/into the hand part of the electric toothbrush and/or can insert his own toothpaste bag. It may happen here that the toothpaste bags are replaced before being completely empty and that toothpaste bags that have only been filled partially and have already been used are used.

EP 0930960 B1 describes a device for body care having a cassette which contains an auxiliary liquid. The cassette is provided with a key, which enables a function of the device when the cartridge is linked to the device.

SUMMARY

In one aspect, an application substance reservoir, e.g., a toothpaste bag, has a data carrier with a data memory which can be read and written to by a suitable toothbrush. A suitable toothbrush has a data receiver for reading the data stored in the data carrier and a data transmitter for writing to the data carrier. In this way, there may be a transfer of data between the application substance reservoir and the toothbrush, whereby the data read by the data receiver may be used by a control unit present in the toothbrush, e.g., for display of the filling level in the application substance reservoir and/or for adaptation of the toothbrush operation to the particular application substance used.

The data transmitter may preferably be used to store updated filling level data characterizing the remaining amount of application substance in the application substance reservoir, so that the updated filling level data is not stored in the toothbrush but instead is stored in the data memory of the application substance reservoir. This has the advantage that the filling level data are not lost when the application substance reservoir is replaced, e.g., because another user of the toothbrush wants to use his/her own toothpaste. If the application substance reservoir that has been replaced is inserted back into the toothbrush, the toothbrush may read out and/or display the filling level stored in the data memory of the application substance reservoir.

Additional data may advantageously be stored in the data memory of the application substance reservoir and may be utilized by the control unit to control other functions. For example, a user-specific data profile, which may be entered by the control unit on insertion of the application substance reservoir or each time the toothbrush is turned on, may be stored in the data carrier of the application substance reservoir, for example, so that operation of the toothbrush is individually adaptable for the respective user. For example, this may be a tooth-brushing time which the respective user would like to maintain with the special toothpaste. Other operating parameters of an electric toothbrush such as the drive speed, greeting tone, oscillation frequency, etc., may also be adjusted as a function of the saved user-specific data.

The data carrier on the application substance reservoir may advantageously also contain control data preselected by the manufacturer on the basis of which the control unit of the toothbrush activates, controls or changes toothbrush functions. In the simplest case, these data may characterize the full status or the contents of the application substance reservoir, and the control unit may trigger a display device on the toothbrush by means of these data to display the filling level and/or the amount of application substance used. However, on the basis of the corresponding data, other operation-relevant components, in particular the drive and/or a conveyance device may be used for dispensing the application substance. For example, an application substance-specific metered quantity may be stored in the data carrier, this quantity being used to trigger the conveyance device, so that the conveyance device dispenses the predetermined quantity of application substance. In a further embodiment, data for controlling the drive mode of the toothbrush may also be stored in the data carrier; in particular, the control unit may also switch the toothbrush drive to a tooth-brushing mode on the basis of the data read out of the data carrier of the application substance reservoir, when the application substance reservoir contains a toothpaste, while the drive device is switched to a polishing mode when the application substance reservoir contains a polishing agent.

In a preferred embodiment, the toothbrush may be enabled with the help of data stored in the data carrier. In the control unit, an enabling function may be provided, allowing the enabling of toothbrush operation and/or individual operating functions as a function of the data received by the data carrier. In this way it is possible to prevent, for example, the toothbrush from inadvertently being switched to operating mode without inserting the application substance reservoir. Likewise, it is possible to prevent the toothbrush from being operated when an unsuitable application substance is inserted; in the case of application substances that are too viscous, for example, this might result in damage to the conveyance device.

The data carrier on the application substance reservoir as well as the data transfer means may be designed in various ways. The data receiver and/or the data transmitter preferably operate without contact. In a simple embodiment, the data carrier may have a magnet and the data receiver may have a reed sensor by means of which the magnet can be gripped on the application substance reservoir. If the application substance reservoir has been inserted, then the reed sensor will detect a pulse which charges a counter in the control unit at a value which corresponds to the full status of the application substance reservoir in a counter. If application substance is subsequently dispensed during operation, the amount of substance is decremented on the counter accordingly and the respective filling level of the application substance reservoir may be displayed. However, such a display yields correct values only when the application substance reservoir is full when inserted.

Preferably, however, a writable data carrier is provided on the application substance reservoir. In particular, a transponder chip may be provided, which can communicate with a suitable data transceiver in the toothbrush. In some implementations, a so-called RFID chip, i.e., a radiofrequency identification chip, may be provided as the data carrier; the RFID chip communicates with the data transceiver of the toothbrush in the frequency range of approx. 13.56 MHz.

However, other embodiments of the data carrier and the data transfer means are of course also possible. For example, the data carrier may have optical coding, which can be read by an optical sensor in the toothbrush. Likewise, an electric, inductive and/or magnetic design of the data carrier and/or the data transfer means is also possible.

In a preferred embodiment, the data transceiver of the toothbrush is a radio transceiver having multiple antennas for communication with multiple data carriers. Two completely separate data transceivers may of course be provided in a toothbrush to communicate with multiple data carriers. A substantial cost saving, however, is achieved by the fact that multiple antennas are operated with only one data transceiver. The data transceiver preferably comprises a switching device which optionally activates one antenna or the other. The antennas are preferably designed so that the one antenna can communicate with the data carrier on the application substance reservoir while the other antenna can communicate with a data carrier on a replaceable attachable brush of the toothbrush. In this way, data from the application substance reservoir can be input on the one hand to control operation of the toothbrush as a function of the application substance in the manner described previously, while on the other hand data may also be input from the respective attachable toothbrush to suitably control the operation of the toothbrush as a function thereof.

DETAILED DESCRIPTION

Figure 1:
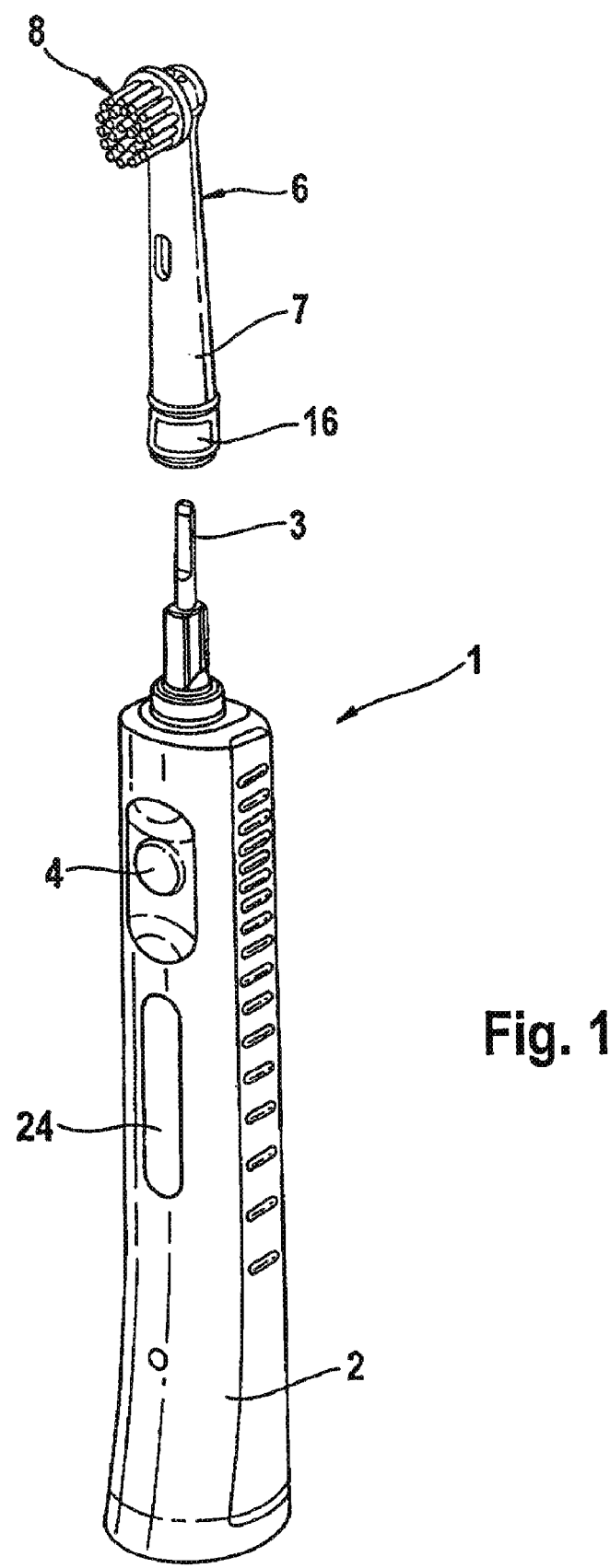
FIG. 1 shows a schematic diagram of an electric toothbrush.
Figure 3:
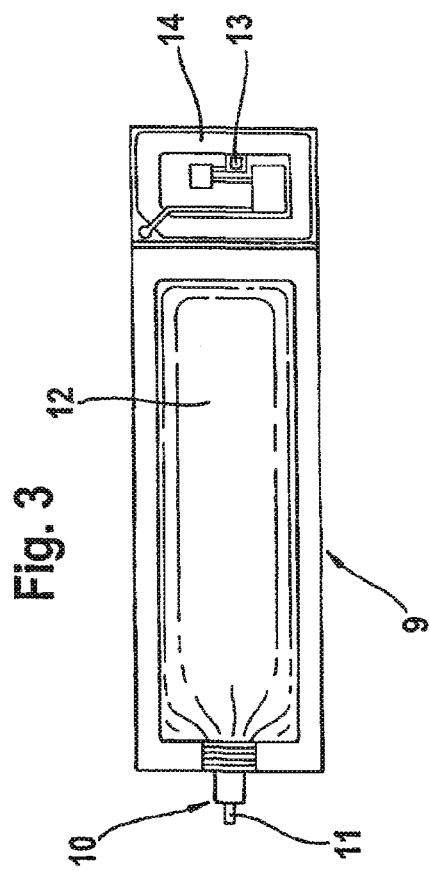
FIG. 3 shows a top view of an application substance reservoir with a transponder code which is applied to an appendage of the application substance reservoir.
Figure 4:
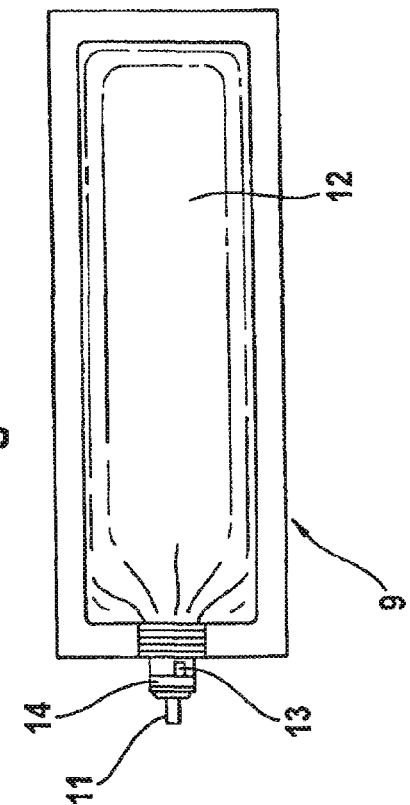
FIG. 4 shows a top view of an application substance reservoir with a transponder chip which is mounted on the connecting means of the application substance reservoir.
Figure 2:
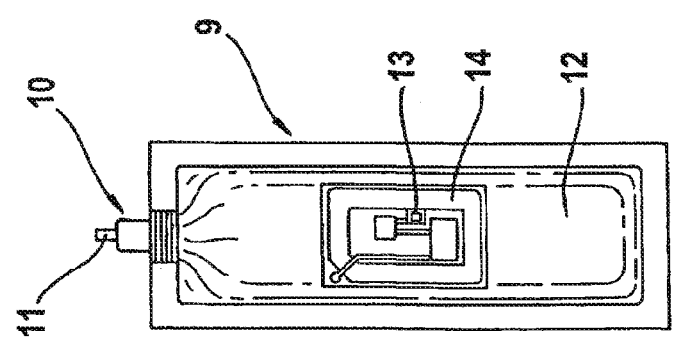
FIG. 2 shows a top view of an application substance reservoir for an electric toothbrush having a transponder chip for data communication with the toothbrush.

FIG. 1 illustrates an electric toothbrush 1 having a hand part 2 that contains a drive motor which drives a driveshaft 3 protruding out of the hand part 2 at one end in an essentially known manner. In addition, the hand part 2 contains a control unit, preferably electronic, that controls the operation of the toothbrush 1 including the drive motor. An on/off switch 4 is provided on the hand part 2. A replaceable attachable brush 6 having a brush tube 7 which carries a bristle field 8 may be attached to the driveshaft 3 in an essentially known manner. An application substance reservoir 9, preferably a toothpaste bag as illustrated in FIGS. 2 through 4 may be inserted into the hand part 2. A conveyance device (not shown in FIG. 1), which may comprise a pump driven by the drive motor, for example, to dispense the toothpaste stored in the toothpaste bag 9 by motor drive is provided in the hand part 2. The corresponding conveyance lines (also not shown in FIG. 1) may lead into the attachable brush 6 to dispense the toothpaste on the bristle field 8.

The toothpaste bag 9 comprises a connector 10, which is adapted to the conveyance unit of the toothbrush and with the help of which the bag can be connected to the suitably designed connection interface of the conveyance device, so that the interior of the toothpaste bag 9 has a flow connection to the conveyance device. The connector 10 has a tubular connection 11 which is welded into the bag body 12, preferably made of a film, and protrudes out of the bag body for a distance. The connection 11 may be connected to the complementary connection interface on the conveyance device end so that toothpaste can be conveyed out of the interior of the bag body 12. Moreover the toothpaste bag 9 is itself adapted in its shape to the housing of the toothbrush, in particular to the bag receptacle space in/on the toothbrush. A data carrier 13 consisting of a transponder chip, which is connected to a data transfer device 14 is provided on the toothbrush bag 9. The data transfer device 14 may have an antenna in the form of a magnetic coil to exchange data with the control unit in the hand part 2.

Figure 5:
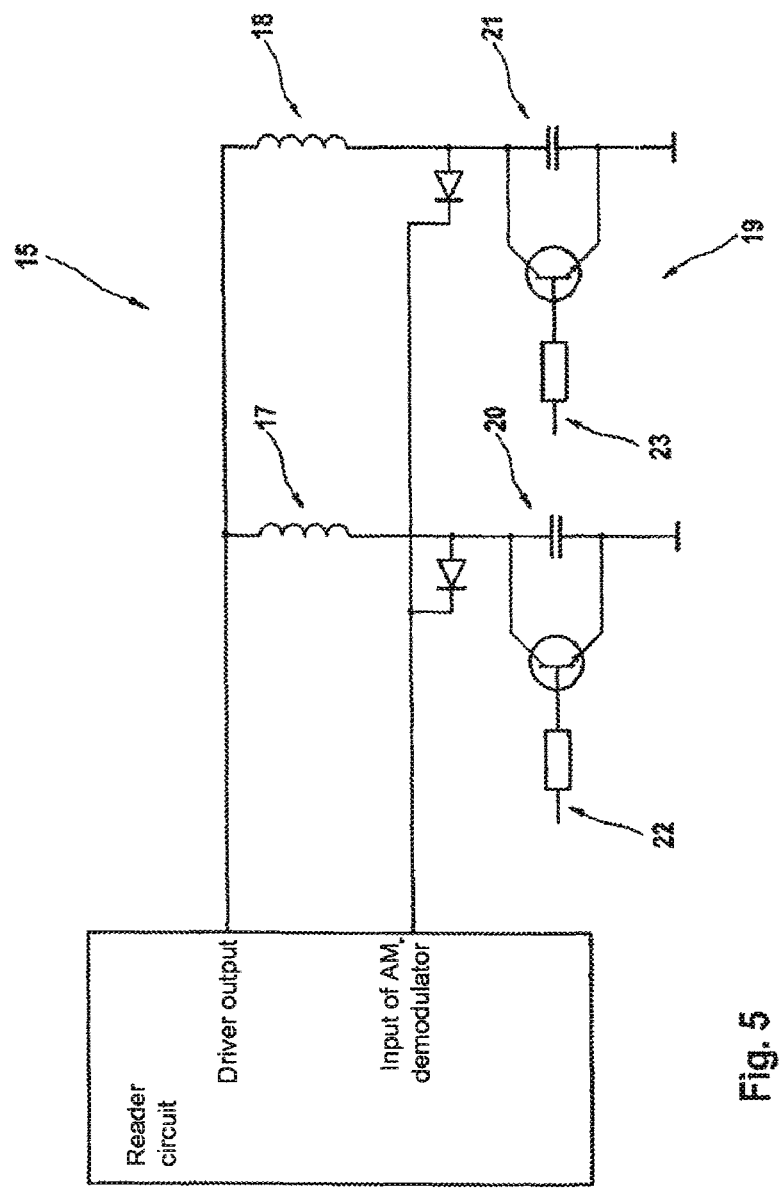
FIG. 5 shows a schematic diagram of the data transceiver of a toothbrush for communicating with the data carrier on the application substance reservoir and a data carrier on an attachable brush.

The control unit in the hand part 2 also has a data transfer device 15 which is depicted in FIG. 5 and also has a data transceiver. The data transceiver has two separate antennas so that the control unit can communicate not only with the data carrier 13 on the toothpaste bag 9 but also with a corresponding data carrier 16 on the brush tube 7 of the attachable brush 6. The data carrier 16 on the attachable brush 6 is preferably also a transponder chip. The data transfer device 15 contains two antenna coils 17 and 18 which may optionally be activated by means of a switching device 19. The one antenna coil 17 is provided for communication with the data carrier 16 on the attachable brush 6, while the other antenna coil 18 is provided for communication with the data carrier 13 on the toothpaste bag 9. The switching device 19 comprises two transistors, which can be controlled by the control unit of the hand part 2 via inputs 22, 23. Depending on which transistor is triggered, one of the antenna coils 17, 18 is deactivated by short-circuiting a respective resonant-circuit capacitor 20, 21 by the transistor. Therefore, no resonance sharpness of the voltage in the respective resonant circuit can develop, while the current in the resonant circuit remains low and practically no power can be emitted and/or no signal received.

Various toothbrush functions can be controlled via the data stored in the data carrier 13 of the toothpaste bag 9. First, the control unit may trigger a display device, e.g., in the form of a display 24, as a function of the data input to display the type of toothpaste inserted, for example, and/or the filling level in the application substance reservoir 9. However, data may also be stored in the data carrier 13, influencing the drive mode of the drive motor and/or the operation of the conveyance device. For example, the drive may be switched between a polishing mode and a tooth-brushing mode, depending on the data input from the toothpaste bag. Depending on the data input, the conveyance device may dispense different quantities of toothpaste, which are specific for the respective toothpaste. Likewise, enabling of any toothbrush functions can also be implemented. To this end, an enable function is provided in the control unit, enabling the operation of the toothbrush only when the "correct" code has been input by the data carrier 13 and/or 16 of the toothbrush bag 9 and/or the attachable brush 6.

In addition, the control unit of the hand part 2 may also store filling level data in the data carrier 13 of the toothbrush bag 9. To do so, on insertion of a toothbrush bag, the control unit will first read out the filling level stored there, but this level is then reduced each time the toothbrush is operated, decreasing it by an amount that depends on consumption. The prevailing filling level or the amount of application substance consumed is transmitted to the data carrier 13 of the toothbrush bag 9 when operation of the toothbrush stops, so that when operation of the toothbrush is resumed again or after changing and replacing the toothbrush bag 9, the prevailing filling level is stored there and thus the filling level display is displayed correctly even when the application substance reservoir inserted into the toothbrush is not completely full.

User-specific data may advantageously also be stored in the data carrier 13 to control the operation of the toothbrush in a user-specific manner as a function of the stored data. This is appropriate, for example, when the hand part 2 is used by multiple users who use different application substances. However, even when the same toothbrush bag is being used, user-specific data may still be stored in the data carrier 13. For example, different toothpaste dispensing quantities may be defined for different users, so that each user receives the amount of toothpaste he/she desires. Even if only one user is defined, different dispensing amounts may be defined for morning and evening, for example. Other operating parameters such as the drive speed, drive mode, etc., may be stored in the data carrier 13 in a user-specific manner.

In another embodiment, multiple application substance reservoirs or one application substance reservoir having multiple receptacle chambers may be used for dispensing different application substances, in which case two conveyance devices are then advantageously provided in the toothbrush. In this case, a mixing ratio of the two application substances may also be stored in the data carrier 13 or in the data carriers 13 so that the two conveyance devices are operated in a suitable drive mode to achieve the desired mixing ratio.

According to an especially advantageous embodiment, a complete data record or a part thereof is read into the control unit on insertion of the toothpaste bag into the hand part 2 and is stored in the data carrier 13 of the toothpaste bag 9. Control updates may also subsequently be fed into the hand part 2, thereby supplementing or modifying the control functions in the hand part 2 without the toothbrush owner having to seek out a suitable service shop to do so.

The invention claimed is:

1. An application substance reservoir for a toothbrush, the reservoir comprising:
    a body which may be filled with toothpaste or another application substance, and
    a data carrier readable by the toothbrush and having a data memory that is writable by the toothbrush,
    wherein the data carrier contains data for activation and/or control of at least one function of the toothbrush.

2. The application substance reservoir according to claim 1, wherein the data carrier comprises a transponder chip.

3. The application substance reservoir according to claim 1, wherein the data carrier has a magnet.

4. The application substance reservoir according to claim 1, wherein the data carrier contains data about the filling level of the application substance in the application substance reservoir.

5. The application substance reservoir according to claim 1, wherein the data carrier contains user-specific data.

6. The application substance reservoir according to claim 1, wherein the data carrier contains at least a part of a control program.

7. The application substance reservoir according to claim 6, wherein the control program comprises a software update for the operation of the toothbrush.

8. The application substance reservoir according to claim 1, wherein the data carrier is provided with a data transfer device.

9. An electric toothbrush comprising:
    a body configured to receive a replaceable application substance reservoir;
    a data receiver for reading data contained in a data carrier which is mounted on the replaceable application substance reservoir and
    a data transmitter configured to write on the data carrier.

10. The electric toothbrush according to claim 9, further comprising a control unit which controls the toothbrush as a function of the data read.

11. The electric toothbrush according to claim 10, wherein the control unit is configured to control the operation of the toothbrush as a function of data read out of the data carrier and/or activates and/or alters at least one control function of the toothbrush.

12. The electric toothbrush according to claim 11, further comprising a conveyance device for delivering a substance from the reservoir to a user, wherein the control unit is configured to control the conveyance device as a function of data read out of the data carrier.

13. The electric toothbrush according to claim 11, further comprising a brush drive, wherein the control unit is configured to control the brush drive as a function of data read out of the data carrier.

14. The electric toothbrush according to claim 10, wherein an enable function is stored in the control unit, triggering or refusing to enable operation of the toothbrush and/or individual operating functions of the toothbrush as a function of the data received by the data carrier.

15. The electric toothbrush according to claim 10 wherein the control unit is configured to read at least part of a control program from the data carrier.

16. The electric toothbrush according to claim 10, wherein the control unit comprises a receiver configured to receive receiver data from multiple data carriers.

17. The electric toothbrush according to claim 16 wherein the receiver comprises multiple antennas.

18. The electric toothbrush according to claim 17, further comprising a switching device configured to selectively activate the antennas.

19. The electric toothbrush according to claim 10, wherein the control unit is configured to activate and/or alter at least one control function of the toothbrush.

20. The electric toothbrush according to claim 9, wherein at least one of the data receiver and the data transmitter is configured to transmit data in a noncontact manner.

21. The electric toothbrush according to claim 9, wherein the data receiver has a reed sensor for detecting a magnet.

22. The electric toothbrush according to claim 9, further comprising a display device which is controllable as a function of data stored in the data carrier.

23. The electric toothbrush according to claim 22 wherein the display device is configured to display the filling-level in the reservoir based on the data read out of the data carrier.

24. The electric toothbrush according to claim 9, wherein the data transmitter transmits the amount of application substance applied and/or the amount of application substance remaining in the application substance reservoir to the data carrier.

25. An application substance reservoir for a toothbrush, the reservoir comprising:
   a body which may be filled with toothpaste or another application substance, and
   a data carrier readable by the toothbrush and having a data memory that is writable by the toothbrush,
   wherein the data carrier contains user-specific data.

* * * * *